US007608408B2

(12) United States Patent
Burton et al.

(10) Patent No.: US 7,608,408 B2
(45) Date of Patent: Oct. 27, 2009

(54) METHODS OF IDENTIFYING COMPOUNDS THAT INHIBIT NOTCH CLEAVAGE

(75) Inventors: Catherine Burton, Durham, CT (US); Charles F. Albright, New Jersey, CT (US); Judith A. Wardwell-Swanson, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 179 days.

(21) Appl. No.: 11/595,721

(22) Filed: Nov. 10, 2006

(65) Prior Publication Data

US 2007/0105161 A1    May 10, 2007

Related U.S. Application Data

(60) Provisional application No. 60/735,272, filed on Nov. 10, 2005.

(51) Int. Cl.
*C12Q 1/68* (2006.01)
*C07K 14/435* (2006.01)
*G01N 33/53* (2006.01)
*G01N 33/68* (2006.01)

(52) U.S. Cl. .......................... 435/7.1; 435/6; 435/7.92; 436/501; 530/350

(58) Field of Classification Search ........................ None
See application file for complete search history.

(56) References Cited

OTHER PUBLICATIONS

Barten et al. Gamme secretase inhibitors for Alzheimer's disease. Drugs R D 7(2): 87-97, 2006.*
Sekine et al. Hath1 up-regulates gastric mucin gene expression in gastric cells. Biochem Biophys Res Comm 344: 1166-1171, 2006.*
Gaudier et al. Butyrate specifically modulates MUC gene expression in intestinal epithelial goblet cells deprived of glucose. Am J Physiol Gastrointest Liver Physiol. 287(6):G1168-1174, 2004.*
Smirnova et al. LPS up-regulates mucin and cytokine mRNA expression and stimulates mucin and cytokine secretion in goblet cells. Cell Immunol 221(1): 42-49, 2003.*
Smirnova et al. Up-regulation of mucin secretion in HT29-MTX cells by the pro-inflammatory cytokines tumor necrosis factor-alpha and interleukin-6. Eur Cytokine Network 12(1): 119-125, 2001.*
Velcich et al. Patterns of expression of lineage-specific markers during the in vitro-induced differentiation of HT29 colon carcinoma cells. Cell Growth Differ 6(6): 749-757, 1995.*
Iwashita et al. mRNA of MUC2 is stimulated by IL-4, IL-13 or TNF-alpha through a mitogen-activated protein kinase pathway in human colon cancer cells. Immunol Cell Biol 81(4): 275-282, 2003.*
McCool et al. Regulated and unregulated pathways for MUC2 mucin secretion in human colonic LS180 adenocarcinoma cells are distinct. Biochem J 312: 125-133, 1995.*
Prasad et al. Discovery of (S)-2-((S)-2-(3,5-difluorophenyl)-2-hydroxyacetamido)-N-((S,Z)-3-methyl-4-oxo-4,5-dihydro-3H-benzo[d][1,2]diazepin-5-yl)propanamide (BMS-433796): a gamma-secretase inhibitor with Abeta lowering activity in a transgenic mouse model of Alzheimer's disease. Bioorg Med Chem Lett 17: 4006-4011, 2007.*
Goldstein et al. Ex vivo occupancy of gamma-secretase inhibitors correlates with brain beta-amyloid peptide reduction in Tg2576 mice. J Pharmcol Ecp Therap 323(1): 102-108, 2007.*
Chiang, M. Y., et al, "Activated Notch takes center stage in T-cell leukemogenesis", Eur. J. of Hum. Genet., vol. 13, pp. 393-398 (2005).
De Strooper, B., Aph-1, Pen-2, and Nicastrin with Presenilin Generate an Active γ-Secretase Complex, Neuron, vol. 38, pp. 9-12 (2003).
DeBiasio, R. L., et al., "Myosin II Transport, Organization, and Phosphorylation: Evidence for Cortical Flow/Solation-Contraction Coupling during Cytokinesis and Cell Locomotion", Mol. Bio. Cell, vol. 7, pp. 1259-1282 (1996).
Doerfler, P., et al., "Presenilin-dependent γ-secretase activity modulates thymocyte development", Proc. Natl. Acad. Sci., vol. 98, pp. 9312-9317 (2001).
Farkas, D. L., et al., "Multimode Light Microscopy and the Dynamics of Molecules, Cells, and Tissues", Annu. Rev. Physiol., vol. 55, pp. 785-817 (1993).
Giuliano, K. A., et al., "Fluorescent Protein Biosensors: Measurement of Molecular Dynamics in Living Cells", Annu. Rev. Biophys. Biomol. Struct., vol. 24, pp. 405-434 (1995).
Giuliano, K. A., et al., "Measurement and manipulation of cytoskeletal dynamics in living cells", Curr. Op. Cell Bio., vol. 7, pp. 4-12 (1995).
Hadland, B. K., et al., "γ-Secretase inhibitors repress thymocyte development", Proc. Natl. Acad. Sci., vol. 98, pp. 7487-7491 (2001).
Hahn, K., et al., "Patterns of elevated free calcium and calmodulin activation in living cells", Nature, vol. 359, pp. 736-739 (1992).

(Continued)

*Primary Examiner*—Bridget E Bunner
(74) *Attorney, Agent, or Firm*—Melissa Handler

(57) ABSTRACT

In vitro cell-based methods for identifying compounds that inhibit Notch cleavage and methods for identifying γ-secretase inhibitors that exhibit reduced induction of goblet cell metaplasia are provided. Also provided are methods of identifying compounds that inhibit cleavage of γ-secretase substrates other than Notch and homogeneous compositions or cultures of Notch-expressing cells that undergo mucin-2 or mucin-5AC induction in response to a compound known to inhibit Notch cleavage and methods of their generation.

8 Claims, 13 Drawing Sheets

OTHER PUBLICATIONS

Hallahan, A. R., et al., "The SmoA1 Mouse Model Reveals That Notch Signaling Is Critical for the Growth and Survival of Sonic Hedgehog-Induced Medulloblastomas", Cancer Res., vol. 64, pp. 7794-7800 (2004).

Heim, R., et al., "Engineering green fluorescent protein for improved brightness, longer wavelengths and fluorescence resonance energy transfer", Curr. Bio., vol. 6, pp. 178-182 (1996).

Jarriault, S., et al., "Signalling downstream of activated mammalian Notch", Nature, vol. 377, pp. 355-358 (1995).

Kopan, R., et al., "Signal transduction by activated mNotch: Importance of proteolytic processing and its regulation by the extracellular domain", Proc. Natl. Acad. Sci., vol. 93, pp. 1683-1688 (1996).

Li, J., et al., "Notch signaling from tumor cells: A new mechanism of angiogenesis", Cancer Cell, vol. 8, pp. 1-3 (2005).

Milano, J., et al., "Modulation of Notch Processing by γ-Secretase Inhibitors Causes Intestinal Goblet Cell Metaplasia and Induction of Genes Known to Specify Gut Secretory Lineage Differentiation", Toxicol. Sci., vol. 82, pp. 341-358 (2004).

Schroeter, E. H., et al., "Notch-1 signalling requires ligand-induced proteolytic release of intracellular domain", Nature, vol. 393, pp. 382-386 (1998).

Selkoe, D., et al., "Notch and Presenilin: Regulated Intramembrane Proteolysis Links Development and Degeneration", Annu. Rev. Neurosci., vol. 26, pp. 565-597 (2003).

van Es, J. H., et al., "Notch/γ-secretase inhibition turns proliferative cells in intestinal crypts and adenomas into goblet cells", Nature, vol. 435, pp. 959-963 (2005).

Waggoner, A., et al., "Multiparameter Fluorescence Imaging Microscopy: Reagents and Instruments", Hum. Pathol., vol. 27, pp. 494-502 (1996).

Weggen, S., et al., "Aβ42-lowering Nonsteroidal Anti-inflammatory Drugs Preserve Intramembrane Cleavage of the Amyloid Precursor Protein (APP) and ErbB-4 Receptor and Signaling through the APP Intracellular Domain", J. Bio. Chem., vol. 278, pp. 30748-30754 (2003).

Weggen, S., et al., "A subset of NSAIDS lower amyloidogenic Aβ42 independently of cyclooxygenase activity", Nature, vol. 414, pp. 212-216 (2001).

Weng, A. P., et al., Activating Mutations of NOTCH1 in Human T Cell Acute Lymphoblastic Leukemia, Science, vol. 306, pp. 269-271 (2004).

Petit, A. et al., "New protease inhibitors prevent γ-secretase-mediated production of Aβ40/42 without affecting Notch cleavage", Nature Cell Biology, vol. 3, pp. 507-511 (2001).

Wong, G. et al., "Chronic Treatment with the γ-Secretase Inhibitor LY-411,575 Inhibits β-Amyloid Peptide Production and Alters Lymphopoiesis and Intestinal Cell Differentiation", The J. of Biological Chemistry, vol. 279(13), pp. 12876-12882 (2004).

\* cited by examiner

Fig. 8B Dog, treated for 3 days (H/E)
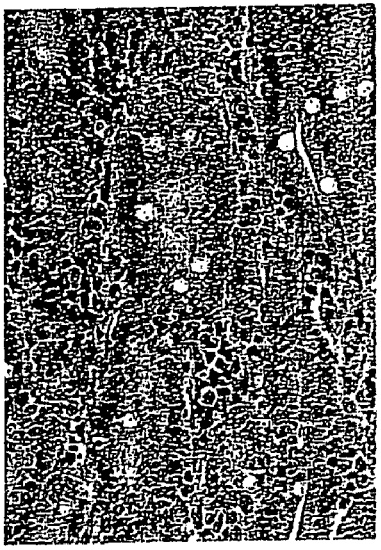
Fig. 8A Dog control duodenum (H/E)
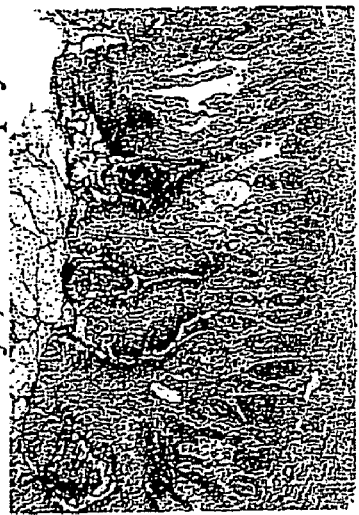
Fig. 8E Rat duodenum, treated 3 days; villus atrophy
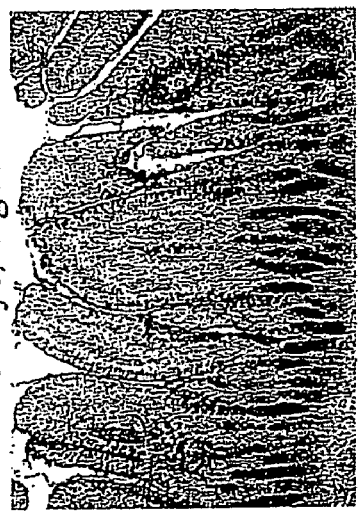
Fig. 8D Rat duodenum, treated 3 days; ↑ goblet cells
Fig. 8C Rat control duodenum (PAS)

METHODS OF IDENTIFYING COMPOUNDS THAT INHIBIT NOTCH CLEAVAGE

This application claims priority to U.S. Provisional Patent Application Ser. No. 60/735,272, filed Nov. 10, 2005, which is hereby incorporated by reference in its entirety.

FIELD OF THE INVENTION

This invention provides that the inhibition of Notch cleavage induces expression of mucin-2 and mucin-5AC. Mucins are markers for intestinal goblet cell phenotype, and increases in mucin-producing cells are characteristic of goblet cell metaplasia (see, e.g., Milano et al., *Toxicol. Sci.*, 82:341-358 (2004); van Es et. al., *Nature*, 435:959-963 (2005)). The invention thus relates generally to methods for identifying compounds that inhibit Notch cleavage in cells by detecting changes in mucin-2 or mucin-5AC induction in the cell in response to contact with the compound, methods for identifying γ-secretase inhibitors that exhibit reduced induction of goblet cell metaplasia, and homogeneous cultures of Notch-expressing cells that undergo mucin-2 or mucin-5AC induction in response to a compound known to inhibit Notch cleavage.

BACKGROUND OF THE INVENTION

Various publications, including patents, published applications, technical articles and scholarly articles are cited throughout the specification. Each of these cited publications is incorporated by reference herein in its entirety.

The Notch protein family is important for cell fate determination during development and tissue homeostasis in the adult. Upon ligand engagement via the Notch ecto-domain, Notch undergoes sequential extracellular and intramembrane processing. The intra-membrane processing of Notch is mediated by γ-secretase. Cleavage of Notch by γ-secretase leads to release of the Notch intracellular domain (NICD). The NICD fragment mediates Notch signaling via translocation to the nucleus, where it regulates expression of several genes. (Jarriault et al., *Nature* 377(6547): 355-358 (1995); Kopan et al., *Proc Natl Acad Sci USA* 93(4):1683-1688 (1996); Schroeter et al., *Nature* 393(6683):382-386 (1998)). In particular, Notch signaling activates transcription of the mammalian homolog of the Drosophila transcription factor hairy-enhancer of split (Hes). Transcriptional activation of Hes1 is mediated by de-repression of CBF1/RBPJk upon binding by NICD in the nucleus. A number of genes whose expression is regulated by NICD mediate cellular differentiation in many neural and non-neural tissues during development, as well as in the adult (Selkoe and Kopan, *Annu. Rev. Neurosci.*, 26:565-597 (2003)).

γ-secretase is a multiprotein complex consisting of presenilin, nicastrin, Aph-1, and Pen-2 that cleaves several substrate proteins in addition to the Notch receptor family (e.g., Notch 1, 2, 3, and 4) including proteins of the amyloid precursor protein (APP) family (e.g., APP, APLP-1, APLP-2) and E- and N-cadherin superfamily, LRP, Nectin-1α, CD44, ErbB4, and Notch ligands including Jagged-2 and Delta-1 (DeStrooper, *Neuron*, 38:9-12 (2003)). The cleavage products of several γ-secretase substrates have been implicated in various disease states, including Alzheimer's Disease and cancer. Cleavage of APP by γ-secretase leads to β-amyloid (Aβ) synthesis, the major component of amyloid plaques in patients suffering from Alzheimer's disease (Id.). Additionally, Notch intracellular domain (NICD) has been linked to tumor angiogenesis (Li and Harris, *Cancer Cell*, 8:1-3 (2005)). Notch1 activation also has been implicated in acute T-cell lymphoblastic leukemia (Chiang and Pear, *Eur. J. Hum. Genet.*, 13:393-398 (2005); Weng et al., *Science*, 306:269-271 (2004)). Notch signaling also has been linked to growth and survival of medulloblastoma cells (Hallahan et al., *Canc. Res.*, 64:7794-7800 (2004)). Inhibition of the Notch pathway, however, has been demonstrated to induce goblet cell differentiation in adenomas in mice carrying a mutation of the Apc tumor suppressor gene (van Es et al., *Nature*, 435:959-963 (2005)).

Complete inhibition of γ-secretase activity has been suggested to cause severe side-effects (Selkoe and Kopan, *Annu. Rev. Neurosci.*, 26:565-597 (2003); Doerfler et al., *Proc Natl. Acad. Sci USA* 98, 9312-9317 (2001); Hadland et al., *Proc Natl. Acad. Sci USA* 98, 7487-7491 (2001)). For example, recent studies showed that γ-secretase inhibitors cause intestinal goblet cell metaplasia in rats (Milano et al., *Toxicol. Sci.*, 82:341-358, 2004). Reagents that selectively inhibit cleavage of a target γ-secretase substrate without affecting cleavage of other γ-secretase substrates are thus desirable. As an example, a subset of nonsteroidal anti-inflammatory drugs (NSAIDs) was shown to decrease the production of Aβ42 (Weggen et al., *Nature* 414:212-216, 2001), without significantly affecting γ-secretase-mediated cleavage of ErbB4 (Weggen et al., *J. Biol. Chem.* 278, 30748-30754, 2003). In particular, compounds which are able to selectively inhibit cleavage of a target γ-secretase substrate with no or minimal inhibition of the cleavage of Notch are attractive and promising as therapeutic reagents. For example, compounds that selectively inhibit cleavage of APP with no or minimal inhibition of Notch cleavage would be candidate compounds for treatment of Alzheimer's disease.

SUMMARY OF THE INVENTION

The present inventors have now identified that inhibition of Notch cleavage results in cellular changes including, for example, induced mucin-2 and mucin-5AC expression. The invention thus relates generally to methods for identifying compounds that inhibit Notch cleavage in cells, methods for identifying γ-secretase inhibitors that exhibit reduced induction of goblet cell metaplasia, and homogeneous cultures of Notch-expressing cells that undergo mucin-2 or mucin-5AC induction in response to a compound known to inhibit Notch cleavage.

In some aspects of the invention are provided methods of identifying compounds that inhibit Notch cleavage, the methods including the steps of contacting Notch-expressing cells with a test compound and detecting mucin-2 induction or mucin-5AC induction in the cells, wherein mucin-2 induction or mucin-5AC induction is indicative of an inhibitor of Notch cleavage. In some preferred embodiments, mucin-2 induction is detected. Preferred methods of detection of mucin-2 or mucin-5AC induction comprise flow cytometry (e.g., FACS) and high content screening.

In some aspects of the invention, the Notch-expressing cells express γ-secretase. In preferred embodiments, the cells are adenoma cells. In more preferred embodiments, the cells are HT29 cells. In some aspects of the invention, the cells, for example HT29 cells, are preselected based on their ability to undergo mucin-2 induction or mucin-5AC induction in response to a compound known to inhibit Notch cleavage. Compounds known to inhibit Notch cleavage include, for example, benzodiazepine, dibenzazepine, and Compound Z.

Also provided by the invention are methods for identifying γ-secretase inhibitors that exhibit reduced induction of goblet cell metaplasia. The methods include steps of contacting Notch-expressing cells with a test γ-secretase inhibitor; detecting mucin-2 induction or mucin-5AC induction in the cells; and determining whether the level of mucin-2 induction or mucin-5AC induction in the cells is less than the level of mucin-2 induction or mucin-5AC induction in control cells caused by a γ-secretase inhibitor known to inhibit Notch cleavage. In the methods of the invention, a lower level of mucin-2 induction or mucin-5AC induction in Notch-expressing cells contacted with the test γ-secretase inhibitor than in control cells caused by a γ-secretase inhibitor known to inhibit Notch cleavage (e.g., Compound Z, benzodiazepine, dibenzazepine) is indicative of a γ-secretase inhibitor that exhibits reduced induction of goblet cell metaplasia. The Notch-expressing cells in the methods of the invention preferably express γ-secretase. In some embodiments, the Notch-expressing cells are HT29 cells. The cells used in the methods of the invention may preferably be preselected based on their ability to undergo mucin-2 induction or mucin-5AC induction in response to a γ-secretase inhibitor known to inhibit Notch cleavage. The methods for identifying γ-secretase inhibitors that exhibit reduced goblet cell metaplasia may further include a step of determining whether the test γ-secretase inhibitor inhibits cleavage of one or more γ-secretase substrates other than Notch, such as but not limited to an amyloid precursor protein, an E-cadherin, a N-cadherin, LRP, Nectin-1α, CD44, ErbB4, Jagged-2, or Delta-1. Such a determining step may be performed prior to, after, or simultaneously with the other steps of the methods of the invention. The methods for identifying γ-secretase inhibitors of the invention may further involve selecting a test γ-secretase inhibitor that inhibits cleavage of amyloid precursor protein and exhibits a reduced induction of goblet cell metaplasia.

Some embodiments of the methods of identifying compounds that inhibit Notch cleavage and methods for identifying γ-secretase inhibitors that exhibit a reduced induction of goblet cell metaplasia of the invention further comprise determining whether a test compound inhibits cleavage of one or more γ-secretase substrates other than Notch. Examples of γ-secretase substrates other than Notch include but are not limited to amyloid precursor proteins, E-cadherins, N-cadherins, LRP, Nectin-1α, CD44, ErbB4, Jagged-2, and Delta-1. The step of determining whether the test compound inhibits cleavage of one or more γ-secretase substrates other than Notch may be performed prior to, after, or simultaneously with the steps of contacting Notch-expressing cells with a test compound and detecting mucin-2 induction or mucin-5AC induction in the cells. In preferred embodiments, the methods further comprise selection of test compounds that inhibit cleavage of amyloid precursor protein. Preferably, the selected test compounds that inhibit cleavage of amyloid precursor protein exhibit no or minimal reduction in cleavage of Notch.

Also provided by the invention are homogeneous compositions or cultures of Notch-expressing cells that undergo mucin-2 or mucin-5AC induction in response to a compound known to inhibit Notch cleavage, such as but not limited to, benzodiazepine, dibenzazepine, or Compound Z. The Notch-expressing cells of the cultures preferably express γ-secretase. The cells of the homogeneous cultures are preferably adenoma cells, more preferably HT29 cells. The homogeneous cell cultures of the invention are preferably obtained by culturing a single cell or subclone. The single cells may be obtained, for example, from a cell population of cells that exhibit a range of inducible mucin-2 or mucin-5AC windows (i.e., cells that exhibit varied levels of mucin-2 or mucin-5AC induction relative to another cell or cells in the population) in response to a compound known to inhibit Notch cleavage. The homogeneous cell cultures of the invention are preferably obtained from the cell that exhibits the highest inducible mucin-2 or mucin-5AC window in response to a compound known to inhibit Notch cleavage. Such a cell may be identified by methods known in the art such as limiting dilution of a cell population followed by FACS analysis of mucin-2 or mucin-5AC induction in response to a compound known to inhibit Notch cleavage.

Other features and advantages of the invention will be apparent from the detailed description and examples that follow.

BRIEF DESCRIPTION OF THE DRAWINGS

FIGS. 8A-E illustrate the duodenal histopathology of rats or dogs treated with a toxic γ-secretase inhibitor which inhibits Notch. The compound-treated animals displayed intestinal goblet cell metaplasia and villus atrophy (FIG. 8B, dog; FIGS. 8D and 8E, rat) relative to untreated controls (FIG. 8A, dog; FIG. 8C, rat).

DETAILED DESCRIPTION OF ILLUSTRATIVE EMBODIMENTS

Definitions

Figure 1A:
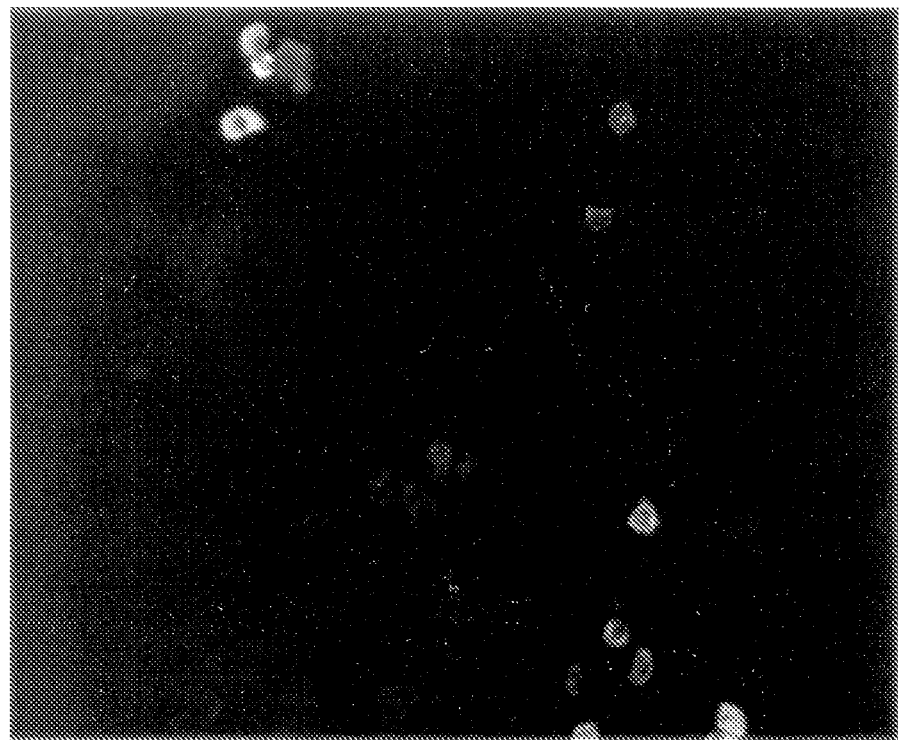
FIGS. 1A and 1B show induction of Mucin-2 (light gray indicating green staining) and -5AC (dark gray indicating red staining) in HT-29 cells but not Mucin-1, -3 or -6 in response to treatment with a γ-secretase inhibitor relative to treatment with vehicle.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The term "about" as used herein when referring to a measurable value such as an amount, a temporal duration, and the like, is meant to encompass variations of ±10% of the specified value, as such variations are appropriate to perform the disclosed methods.

As used herein, the term "contacting" refers to directly or indirectly causing placement together of moieties, such that the moieties directly or indirectly come into physical association with each other, whereby a desired outcome is achieved. Contacting may occur, for example, in any number of buffers, salts, solutions, or in a cell or cell extract. Thus, as used herein, one can "contact" a target cell with a compound as disclosed herein even though the compound and cell do not necessarily physically join together (as, for example, is the case where a ligand and a receptor physically join together), as long as the desired outcome is achieved (e.g., modulation of mucin 2 expression). Contacting thus includes acts such as placing moieties together in a container (e.g., adding a compound as disclosed herein to a container comprising cells for in vitro studies) as well as administration of the compound to a target entity (e.g., injecting a compound as disclosed herein into a laboratory animal for in vivo testing, or into a human for therapy or treatment purposes).

As used herein, the terms "induce" or "induction" refer to a comparative increase in a specified response of a designated material (e.g., expression, enzymatic activity) in the presence of a specified reagent. The reagent is described herein as an "inducer."

As used herein, the terms "inhibit" or "inhibition" refer to a comparative decrease in a specified response of a designated material (e.g., expression, enzymatic activity) in the presence of a specified reagent. The reagent is described herein as an "inhibitor."

As used herein the term, "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reactions that occur within a natural environment.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "γ-secretase inhibitor" refers to a compound that inhibits a biological activity of γ-secretase, for example, the cleavage of one or more γ-secretase substrates including but not limited to proteins of the Notch receptor family (e.g., Notch 1, 2, 3, and 4), the amyloid precursor protein (APP) family (e.g., APP, APLP-1, APLP-2), and E- and N-cadherin superfamily, LRP, Nectin-1α, CD44, ErbB4, and Notch ligands including Jagged-2 and Delta-1.

The term "exhibits reduced induction of goblet cell metaplasia" as used herein refers to a decrease of at least about 10%, at least about 20%, preferably at least about 50%, more preferably at least about 75%, more preferably at least about 80%, even more preferably at least about 90%, even more preferably at least about 95%, and most preferably at least about 99% in the level or degree of mucin-2 or mucin-5AC induction in Notch-expressing cells in response to a compound relative to a control. The control may comprise, for example, the level of mucin-2 or mucin-5AC induction in Notch-expressing cells in the absence of the compound or the level of mucin-2 or mucin-5AC induction in Notch-expressing cells in response to a compound known to inhibit Notch cleavage.

As used herein, "measure" or "determine" refers to any qualitative or quantitative determinations.

"Notch-expressing cell" refers to a cell that contains native or recombinantly expressed Notch protein, for example, at the cell surface.

As used herein, the phrase "no or minimal reduction in cleavage of Notch" refers to a reduction in Notch cleavage by a compound of less than about 25%, preferably less than about 20%, more preferably less than about 10%, more preferably less than about 5%, and most preferably less than about 1% relative to Notch cleavage in the absence of the compound.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. As used herein, any reference herein to a particular protein such as but not limited to γ-secretase, proteins of the Notch receptor family (e.g., Notch 1, 2, 3, and 4), proteins of the amyloid precursor protein (APP) family (e.g., APP, APLP-1, APLP-2), proteins of the E- and N-cadherin superfamily, LRP, Nectin-1α, CD44, ErbB4, and Notch ligands including Jagged-2 and Delta-1, includes functional equivalents thereof. A protein is considered a functional equivalent of reference protein for a specific function if the equivalent protein shares at least one biological activity of the reference protein and is immunologically cross-reactive therewith. Examples of the shared biological activity include enzymatic activity (e.g., protease activity), modulation of transcription of target genes, and activation of downstream effectors. The equivalent may, for example, be a fragment of the reference protein, a derivative of the reference protein, or a mutant of the reference protein (e.g., a substitution, addition, or deletion mutant). For example, it is possible to substitute amino acids in a sequence with equivalent amino acids. Groups of amino acids known normally to be equivalent are:

(a) Ala(A), Ser(S), Thr(T), Pro(P), Gly(G);
(b) Asn(N), Asp(D), Glu(E), Gln(Q);
(c) His(H), Arg(R), Lys(K);
(d) Met(M), Leu(L), Ile(I), Val(V); and
(e) Phe(F), Tyr(Y), Trp(W).

The equivalent protein will normally have substantially the same amino acid sequence as the reference protein. An amino acid sequence that is substantially the same as another sequence, but that differs from the other sequence by means of one or more substitutions, additions and/or deletions is considered to be an equivalent sequence. Preferably, less than 25%, more preferably less than 10%, and most preferably less than 5% of the number of amino acid residues in the amino acid sequence of the reference protein are substituted, added, or deleted.

As used herein, "test compound" refers to any purified molecule, substantially purified molecule, molecules that are one or more components of a mixture of compounds, or a mixture of a compound with any other material that can be analyzed using the methods of the present invention. Test compounds can be organic or inorganic chemicals, or biomolecules, and all fragments, analogs, homologs, conjugates, and derivatives thereof. Biomolecules include proteins, polypeptides, nucleic acids, lipids, polysaccharides, and all fragments, analogs, homologs, conjugates, and derivatives thereof. Test compounds can be of natural or synthetic origin, and can be isolated or purified from their naturally occurring sources, or can be synthesized de novo. Test compounds can be defined in terms of structure or composition, or can be undefined. The compound can be an isolated product of unknown structure, a mixture of several known products, or an undefined composition comprising one or more compounds. Examples of undefined compositions include cell and tissue extracts, growth medium in which prokaryotic, eukaryotic, and archaebacterial cells have been cultured, fermentation broths, protein expression libraries, and the like.

Notch-Expressing Cells, Compositions, and Selection Thereof

Notch-expressing cells are employed in the methods of the invention. The Notch-expressing cells preferably express γ-secretase. The Notch-expressing cells are preferably preselected based on their ability to undergo mucin-2 or mucin-5AC induction in response to a compound known to inhibit Notch cleavage. Compounds known to inhibit Notch cleavage include but are not limited to benzodiazepine, dibenzazepine, and Compound Z:

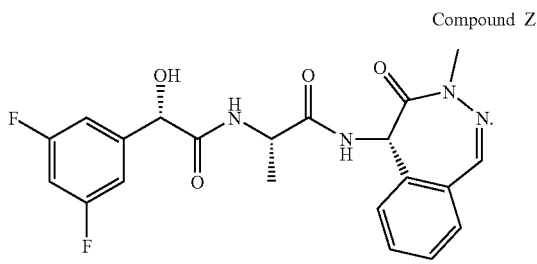

Compound Z

For example, single cells of a cell population may be selected for use in the methods of the invention. Single cells of a cell population may be subcloned by any method known in the art such as but not limited to limiting dilution. Limiting dilution is a procedure for separating cells based on the assumption that if a suspension of cells is diluted with sufficient culture medium, a concentration of cells will be produced such that an accurately measured volume of the diluted suspension will contain a single cell. The single cell may then be cultured to yield a homogeneous composition or culture of cells that exhibit a given characteristic(s). For example, the homogeneous culture of cells may contain cells that exhibit a particular response to a compound, such as cells that exhibit the greatest level of mucin-2 or mucin-5AC induction or highest inducible mucin-2 or mucin-5AC window in response to a compound known to inhibit Notch cleavage relative to that exhibited by the parental cell population and/or to other subclones. "Highest inducible mucin-2 or mucin-5AC window" as used herein refers to strong induction of mucin-2 or mucin-5AC in the presence of the compound coupled with minimal induction in the absence of the compound.

Notch-expressing cells for use in the methods of the invention include adenoma cells such as HT29 cells. Most preferred for use in the methods of the invention are HT29 cells preselected based on their ability to undergo mucin-2 induction or mucin-5AC induction in response to a compound known to inhibit Notch cleavage.

Also provided by the invention are homogeneous compositions or cultures of Notch-expressing cells that undergo mucin-2 or mucin-5AC induction in response to a compound known to inhibit Notch cleavage, such as but not limited to, benzodiazepine, dibenzazepine, or Compound Z. The Notch-expressing cells of the cultures preferably express γ-secretase. The cells of the homogeneous cultures are preferably adenoma cells, more preferably HT29 cells. The homogeneous cell cultures of the invention are preferably obtained by culturing a single cell or subclone. The single cells may be obtained, for example, from a population of cells that exhibit a range of inducible mucin-2 or mucin-5AC windows (i.e., cells that exhibit varied levels of mucin-2 or mucin-5AC induction relative to another cell or cells in the population) in response to a compound known to inhibit Notch cleavage. The homogeneous cell cultures of the invention are preferably obtained from the cell that exhibits the highest inducible mucin-2 or mucin-5AC window in response to a compound known to inhibit Notch cleavage. Such a cell may be identified by methods known in the art such as limiting dilution of a cell population followed by FACS analysis of mucin-2 or mucin-5AC induction in response to a compound known to inhibit Notch cleavage.

Assay Methods

Recent studies have shown that γ-secretase inhibitors cause intestinal goblet cell metaplasia in rats (Milano et al., *Toxicol. Sci.*, 82:341-358, 2004). As demonstrated herein (Example 4), transfection of activated Notch-1 (NICD) bypasses the need for γ-secretase cleavage of Notch and prevents γ-secretase inhibitor-dependent increases in mucin-2 expression. In contrast, activated APP (AICD) does not affect γ-secretase inhibitor-dependent increases in mucin-2 expression (Example 4). Hence, γ-secretase inhibitors cause goblet cell metaplasia by inhibition of Notch cleavage. These facts have been exploited to develop assays for inhibitors of Notch cleavage by γ-secretase.

The invention thus relates generally to methods for identifying compounds that inhibit Notch cleavage in cells. According to the invention, a cell-based assay was developed for identifying compounds that increase mucin-2 or mucin-5AC expression (i.e., induce mucin-2 or mucin-5AC), an indicator of inhibition of Notch cleavage by, for example, γ-secretase.

The invention thus provides methods of identifying compounds that inhibit Notch cleavage, the methods including the steps of contacting Notch-expressing cells with a test compound and detecting mucin-2 induction or mucin-5AC induction in the cells. Induction of mucin-2 or mucin-5AC serves as an indicator of an inhibitor of Notch cleavage. Mucin-2 or mucin-5AC induction may be detected by any means known in the art including but not limited to immunodetection (e.g., ELISA, for example, using antibodies or lectins to mucin-2 or mucin-5AC; Western blot, RIA, immunoprecipitation, immunofluorescence microscopy), flow cytometry (e.g., FACS), and high content screening. Preferred methods for mucin-2 or mucin-5AC detection are flow cytometry and high content screening.

Flow Cytometry

Flow cytometry is a technique for counting, examining, and sorting particles suspended in a stream of fluid. Flow cytometry allows simultaneous multiparametric analysis of the physical and/or chemical characteristics of single cells flowing through an optical/electronic detection apparatus. In flow cytometry analysis, each suspended particle, passing through a beam of light (e.g., a laser light), scatters the light, and fluorescent chemicals in the particle may be excited into emitting light at a lower frequency than the light source. The combination of scattered and fluorescent light is detected and analyzed, thereby permitting analysis of the physical and chemical structure of each individual particle. Flow cytometry methods are generally known in the art. See, e.g., PRAC- TICAL FLOW CYTOMETRY, 4th Edition, Howard M. Shapiro, Wiley Liss, New York, 2003; METHODS IN CELL BIOLOGY: CYTOMETRY, 3rd Edition, Parts A and B, Vols. 63 and 64, Darzynkiewicz, Crissman, Robinson (eds.), Academic Press, San Diego, 2000.

Measurable parameters in flow cytometry include, for example, volume and morphological complexity of cells, cell pigments, DNA (cell cycle analysis, cell kinetics, proliferation etc.), RNA, chromosome analysis and sorting (library construction, chromosome paint), proteins, cell surface antigens, intracellular antigens, nuclear antigens, enzymatic activity, pH, intracellular ionized calcium, magnesium, membrane potential, membrane fluidity, apoptosis, cell viability, and combinations thereof.

Fluorescence-activated cell sorting (FACS) is a type of flow cytometry wherein a suspension of cells is separated into two or more containers, one cell at a time, based upon specific light scattering and fluorescence characteristics of each cell. FACS enables the recovered cells having the characteristic of interest to be cultured.

High Content Screening Assay

Another preferred method of detection of a mucin-2 or mucin-5AC induction is a high content screening (HCS) assay.

A HCS assay combines qualitative observations with quantitative measurements by integrating a cell-based assay (e.g., in a standard 96 or 384 well format) with high resolution fluorescence microscopy with automated image acquisition, specialized image processing algorithms for quantitative single cell analysis, and data and image archiving. HCS enables assessment (e.g., detection, distinction, and quantification) of individual cells or clusters of cells within an array of cells based on preselected parameters. Methods of HCS are known in the art. See, e.g., Ghosh and Haskins, "A Flexible Large-Scale Biology Software Module for Automated Quantitative Analysis of Cell Morphology" in Business Briefings: Future Drug Discovery 2004: 1-4.

Performing a screen on many thousands of compounds requires parallel handling and processing of many compounds and assay component reagents. Standard high throughput screens ("HTS") use mixtures of compounds and biological reagents along with some indicator compound loaded into arrays of wells in standard microtiter plates with 96 or 384 wells. The signal measured from each well, either fluorescence emission, optical density, or radioactivity, integrates the signal from all the material in the well giving an overall population average of all the molecules in the well (U.S. Published application No. 2004/0101912). In contrast to high throughput screens, high-content screens provide more detailed information about the temporal-spatial dynamics of cell constituents and processes, and how they are affected by potential drug candidates (Id.). High-content screens automate the extraction of multicolor fluorescence information derived from specific fluorescence-based reagents incorporated into cells (Giuliano and Taylor (1995), Curr. Op. Cell Biol. 7:4; Giuliano et al. (1995) Ann. Rev. Biophys. Biomol. Struct. 24:405). Cells are analyzed using an optical system that can measure spatial, as well as temporal dynamics. (Farkas et al. (1993) Ann. Rev. Physiol. 55:785; Giuliano et al. (1990) In Optical Microscopy for Biology. B. Herman and K. Jacobson (eds.), pp. 543-557. Wiley-Liss, New York; Hahn et al (1992) Nature 359:736; Waggoner et al. (1996) Hum. Pathol. 27:494).

HCS can be performed on living or fixed cells, using a variety of labeled reporter molecules, such as antibodies, biological ligands, nucleic acid hybridization probes, and multicolor luminescent indicators and "biosensors." The choice of fixed or live cell screens depends on the specific cell-based assay required.

Fixed cell assays are the simplest, since an array of initially living cells in a microtiter plate format can be treated with various compounds and doses being tested, then the cells can be fixed, labeled with specific reagents, and measured. No environmental control of the cells is required after fixation. Spatial information is acquired, but only at one time point. The availability of thousands of antibodies, ligands and nucleic acid hybridization probes that can be applied to cells makes this an attractive approach for many types of cell-based screens. The fixation and labeling steps can be automated, allowing efficient processing of assays.

Live cell assays are more sophisticated and powerful, since an array of living cells containing the desired reagents can be screened over time, as well as space. Environmental control of the cells (temperature, humidity, and carbon dioxide) is required during measurement, since the physiological health of the cells must be maintained for multiple fluorescence measurements over time. There is a growing list of fluorescent physiological indicators and "biosensors" that can report changes in biochemical and molecular activities within cells (Giuliano et al., (1995) Ann. Rev. Biophys. Biomol. Struct. 24:405; Hahn et al., (1993) In Fluorescent and Luminescent Probes for Biological Activity. W. T. Mason, (ed.), pp. 349-359, Academic Press, San Diego).

The types of biochemical and molecular information accessible through fluorescence-based reagents applied to cells include ion concentrations, membrane potential, specific translocations, enzyme activities, gene expression, as well as the presence, amounts and patterns of metabolites, proteins, lipids, carbohydrates, and nucleic acid sequences (DeBiasio et al., (1996) Mol. Biol. Cell. 7:1259; Giuliano et al., (1995) Ann. Rev. Biophys. Biomol. Struct. 24:405; Heim and Tsien, (1996) Curr. Biol. 6:178).

Methods for Identifying γ-Secretase Inhibitors that Exhibit Reduced Induction of Goblet Cell Metaplasia Also provided by the invention are methods for identifying γ-secretase inhibitors that exhibit reduced induction of goblet cell metaplasia. The methods include steps of (a) contacting Notch-expressing cells with a test γ-secretase inhibitor; (b) detecting mucin-2 induction or mucin-5AC induction in the cells; and (c) determining whether the level of mucin-2 induction or mucin-5AC induction in the cells is less than the level of mucin-2 induction or mucin-5AC induction in control cells caused by a γ-secretase inhibitor known to inhibit Notch cleavage. In the methods of the invention, a lower level of mucin-2 induction or mucin-5AC induction in Notch-expressing cells contacted with the test γ-secretase inhibitor than in control cells caused by a γ-secretase inhibitor known to inhibit Notch cleavage (e.g., Compound Z, benzodiazepine, dibenzazepine) is indicative of a γ-secretase inhibitor that exhibits reduced induction of goblet cell metaplasia.

Methods for Identifying Compounds that Inhibit Cleavage of γ-Secretase Substrates Other than Notch The methods of identifying compounds that inhibit Notch cleavage and methods for identifying γ-secretase inhibitors that exhibit reduced goblet cell metaplasia provided herein also may include a step of determining whether a test compound (e.g., a test γ-secretase inhibitor) inhibits cleavage of one or more γ-secretase substrates other than Notch. Examples of secretase inhibitors other than Notch include but are not limited to amyloid precursor proteins, E-cadherins, N-cadherins, LRP, Nectin-1α, CD44, ErbB4, Jagged-2, and Delta-1. The step of determining whether the test compound inhibits cleavage of one or more γ-secretase substrates other than Notch may be performed prior to, after, or simultaneously with the other steps of method. In preferred embodiments, the methods further comprise identification and/or selection of test compounds that inhibit cleavage of amyloid precursor protein. Such test compounds that inhibit cleavage of APP preferably effect no or minimal reduction in cleavage of Notch and/or exhibit reduced induction of goblet cell metaplasia in the methods provided herein.

Any method for determining the ability of a compound to inhibit cleavage of γ-secretase substrates known in the art may be employed. For example, methods for assessing the ability of a compound to cleave APP are known. The ability of a compound to cleave APP may be assessed, for example, by measuring or detecting Aβ peptides (e.g., Aβ1-40, Aβ1-42; see, e.g., U.S. Published Application No. 2003/0215896). Compound Z, for example, demonstrated a Notch cleavage EC50=2.1+/−1.01 nM (n=252) and an APP cleavage EC50=0.81+/−0.33 nM (n=166) in such an assay.

The following examples are provided to illustrate the invention in greater detail. The examples are intended to illustrate, not to limit, the invention.

EXAMPLES

Example 1

Mucin-2 and Mucin-5AC are Induced in HT29 Cells by a γ-Secretase Inhibitor

Figure 1B:
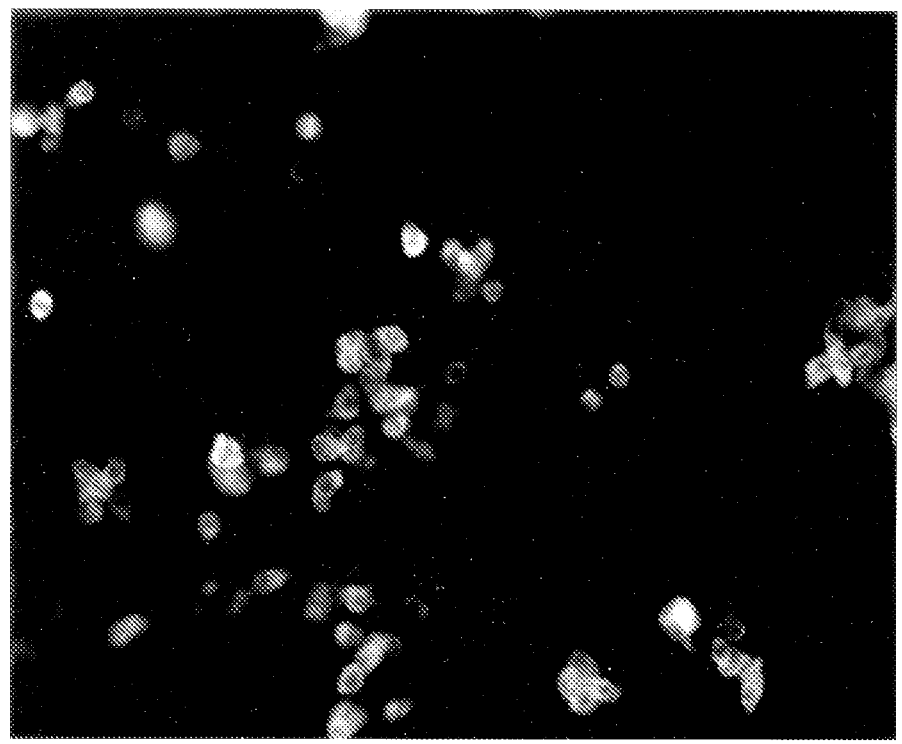

HT29 cells were seeded in 4 or 8 well slide chambers. 24 hours later, cells were treated for 72 hours in serum-free medium with either Compound Z (1 uM in DMSO) or DMSO at a final DMSO concentration of 0.1%. Treated cells were washed twice with PBS, fixed with 4% paraformaldehyde (10 min, RT) followed by methanol (2 min, −20° C.). Fixed cells were washed twice with PBS, incubated with PBS+0.5% TritonX100 for 10 min., washed twice with PBS and blocked for 2 hr in PBS containing 0.1% TritonX100, 2% BSA and 5% dry milk. Cells were stained with primary antibody against mucin-2, mucin-5AC, mucin-1, mucin-3, or mucin-6 by adding primary antibody in blocking buffer and incubating 1 hr, RT. Cells were washed 3× with PBS+0.1% TritonX100 and stained with an appropriate species-specific PE-, TRITC- or FITC-labeled secondary antibody for 30 min., RT. Cells were visualized through microscopy. γ-secretase inhibitor Compound Z induced mucin-2 and mucin-5AC (FIGS. 1A and 1B) but not mucin-1, mucin-3, or mucin-6 in HT29 cells.

Example 2

Selection of an HT29 Subclone

Figure 2:
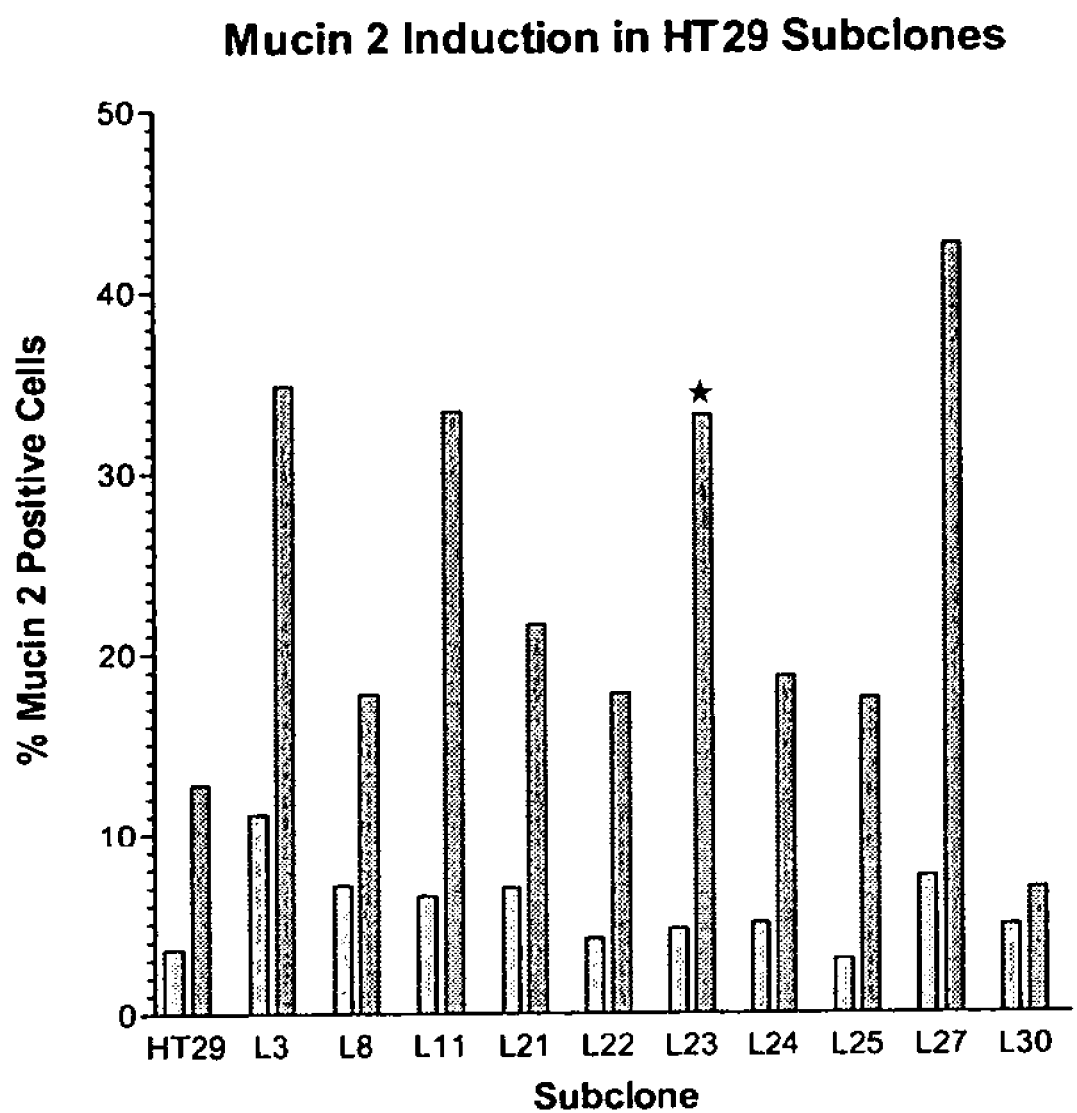
FIG. 2 demonstrates the selection of HT29 subclone L23 for subsequent studies. Subclone L23 exhibited the highest inducible mucin-2 window following contact with Compound Z.
Figure 3A:
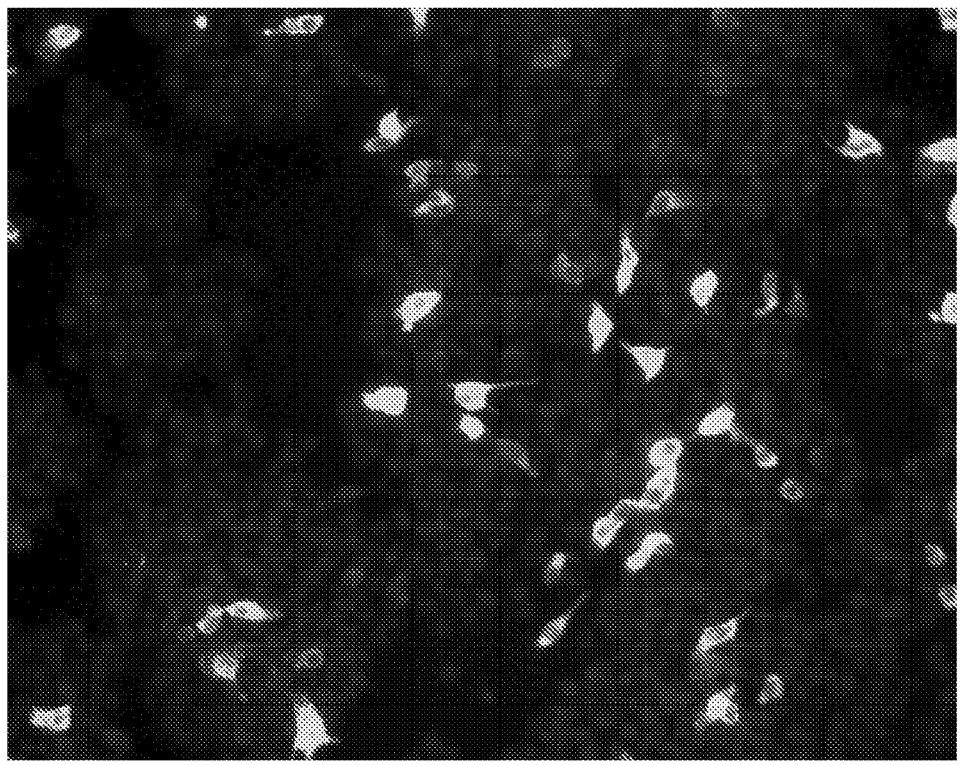
FIGS. 3A and 3B illustrate mucin-2 induction in HT29-L23 by high-content screen assay. Vehicle (FIG. 3A) and Compound Z (1 uM in DMSO) (FIG. 3B)-*treated* HT 29-L23 cells were fixed and stained with nuclear fluorescent dye Hoeshst 33342 (dark gray indicating blue staining) and Mucin-2 antibody followed by an Alexa-488 tagged secondary antibody (light gray indicating green staining). Images were acquired on an ArrayScan system and analyzed for Mucin-2 expression with the Target activation application.
Figure 3B:
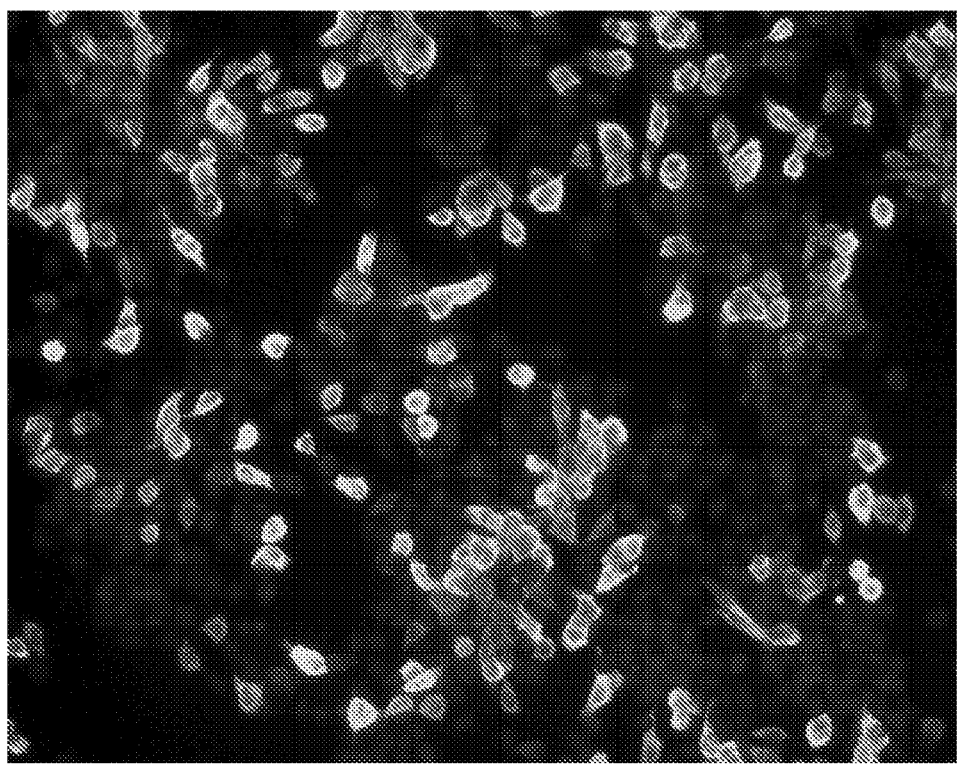

HT29 subclones were generated through limiting dilution. Subclones derived from single cells were treated with Compound Z (1 uM in DMSO) or DMSO for 72 hr. Cells were washed, fixed, and stained with Mucin-2 primary antibody (Cat# V1147, Biomeda Corp) followed by a goat anti-mouse IgG F(ab')$_2$ FITC-labeled secondary antibody (Cat# 115-096-006; Jackson ImmunoResearch) as described in Example 1. Mucin-2 positive cells were measured by FACS analysis (FIG. 2). Alternatively, cells were fixed and stained with nuclear fluorescent dye Hoechst 33342 and mucin-2 antibody followed by an Alexa-488 tagged secondary antibody. Images were acquired on an ArrayScan™ system and analyzed for mucin-2 expression with the Target activation application (FIGS. 3A and 3B). Subclone L23 (HT29-L23) was selected for subsequent studies since it exhibited the highest inducible mucin-2 window.

Example 3

Mucin-2 Induction Correlates with Notch Signaling Potency

HeLa cells were transiently transfected with Notch-1 ΔE and the CBF1 luciferase reporter, and inhibition of Notch signaling by compounds known to inhibit γ-secretase was determined. Induction of mucin-2 in HT29-L23 cells was determined as in Example 1 for the same set of γ-secretase inhibitory compounds. EC50s for inhibition of Notch signaling and mucin-2 induction were determined (Table 1).

TABLE 1

| Compound | HT29-L23 IC50 (nM) | Notch Signaling IC50 (nM) |
|---|---|---|
| 1 (Compound Z) | 11.92 | 4.59 |
| 2 | 26.34 | 13.14 |
| 3 | 46.35 | 50.74 |
| 4 (Compound A) | 0.98 | 0.63 |
| 5 | 253.6 | 120.6 |
| 6 | 194.6 | 99.48 |
| 7 | 149.3 | 68.58 |
| 8 | 76.3 | 15.64 |
| 9 | 42.72 | 40.47 |
| 10 | 261.5 | 60.18 |
| 11 | 129.8 | 24.14 |
| 12 | 68.44 | 67.29 |
| 13 | 59.8 | 34.89 |
| 14 | 54.12 | 65.27 |
| 15 | 257.3 | 67.71 |
| 16 | 228.1 | 82.05 |
| 17 | 70.12 | 38.64 |
| 18 | 42.37 | 39.27 |
| 19 | 33.19 | 21.02 |
| 20 | 56.13 | 25.28 |
| 21 | 47.14 | 52.82 |
| 22 | 63.73 | 43.23 |
| 23 | 92.4 | 62.57 |
| 24 | 99 | 100.6 |
| 25 | 93.72 | 45.73 |
| 26 | 52.94 | 25.11 |
| 27 | 52.87 | 21.04 |

Figure 4:
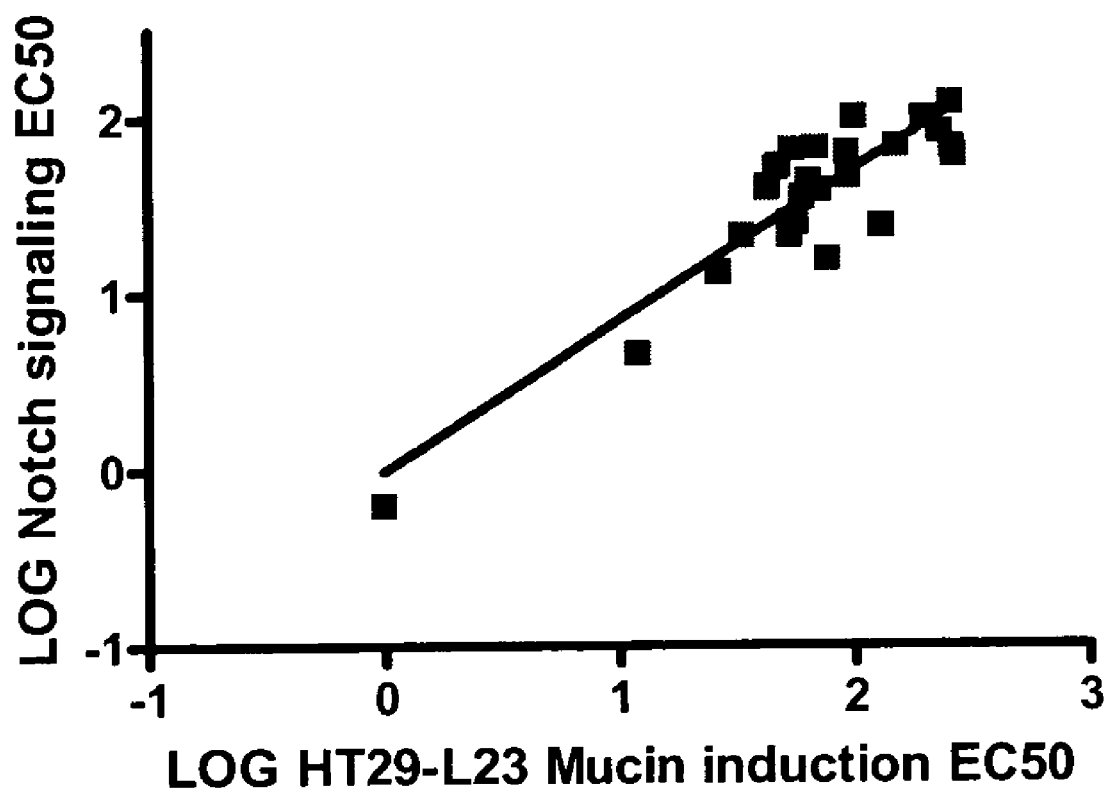
FIG. 4 illustrates the correlation of EC50s for inhibition of Notch signaling in HeLa cells transiently transfected with Notch-1 ΔE and the CBF1 luciferase reporter and Mucin-2 induction in HT29-L23 by γ-secretase inhibitors ($r2=0.79$, $p<0.0001$, $n=27$ compounds; regression line slope=$0.85\pm0.09$).

EC50s for inhibition of Notch signaling and Mucin-2 induction were correlated (r2=0.79, p<0.0001, n=27 compounds; regression line slope=0.85±0.09). Inhibition of Notch signaling in transfected HeLa cells was demonstrated to correlate with mucin-2 induction in HT29-L23 cells (FIG. 4).

Example 4

Effect of Notch Cleavage Inhibitor on Notch Pathway Genes

HT29-L23 cells were treated with Compound Z or DMSO as described in Example 1. mRNA were isolated at indicated time points (FIGS. 5A-E) and analyzed by real time PCR with indicated Taqman probes (Applied Biosystems, Foster City, Calif.). Results were normalized relative to the amount of cyclophilin A (PPIA) mRNA for the same sample and were plotted as fold changes relative to DMSO treated sample at time zero. Statistical significance was determined by one-way ANOVA followed by Bonferroni's multiple comparison test performed within groups.

Figure 5A:
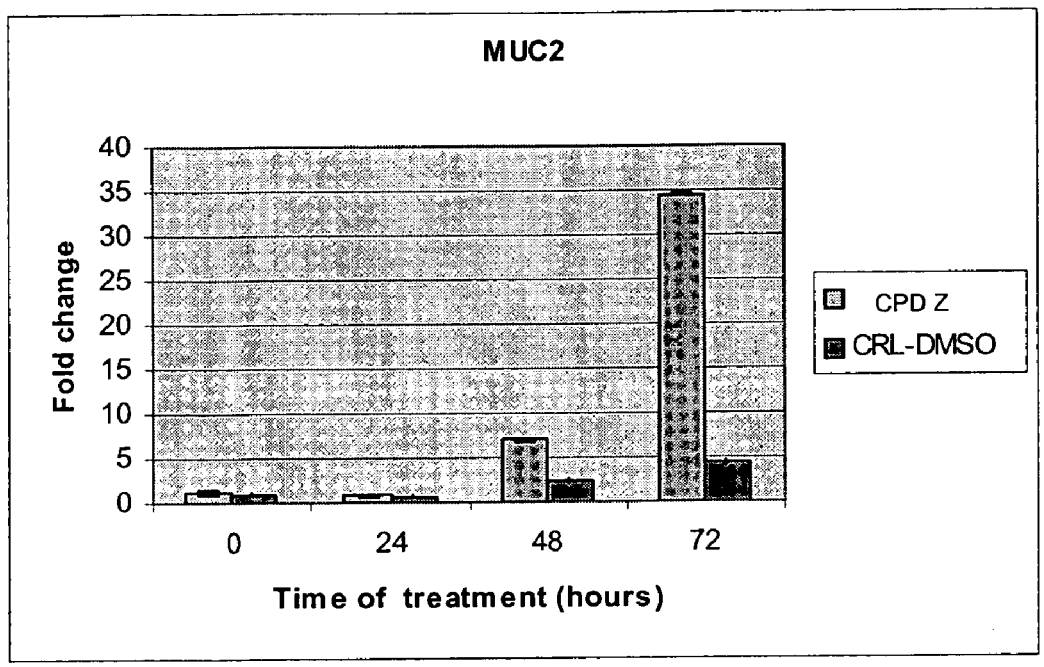
FIGS. 5A-E illustrate the effects on Notch pathway genes by a Notch cleavage inhibitor, Compound Z. Compound Z induces mucin-2 (FIG. 5A), Delta-1 (FIG. 5B), Jagged-2 (FIG. 5C), and Math-1 (FIG. 5D) and downregulates HES-1 (FIG. 5E).
Figure 5B:
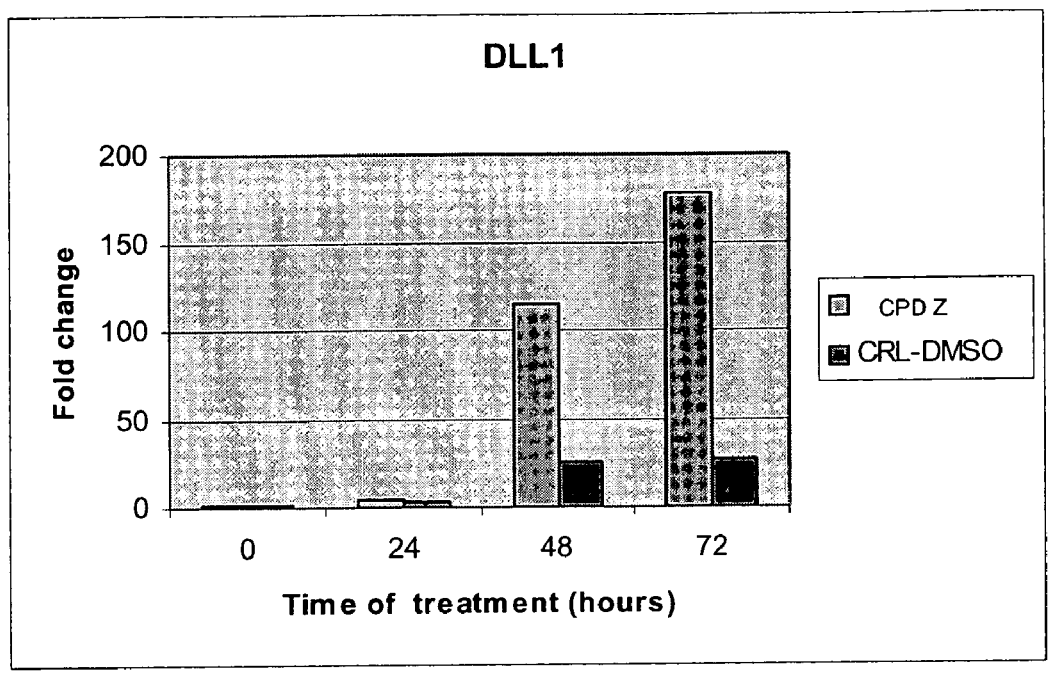
Figure 5C:
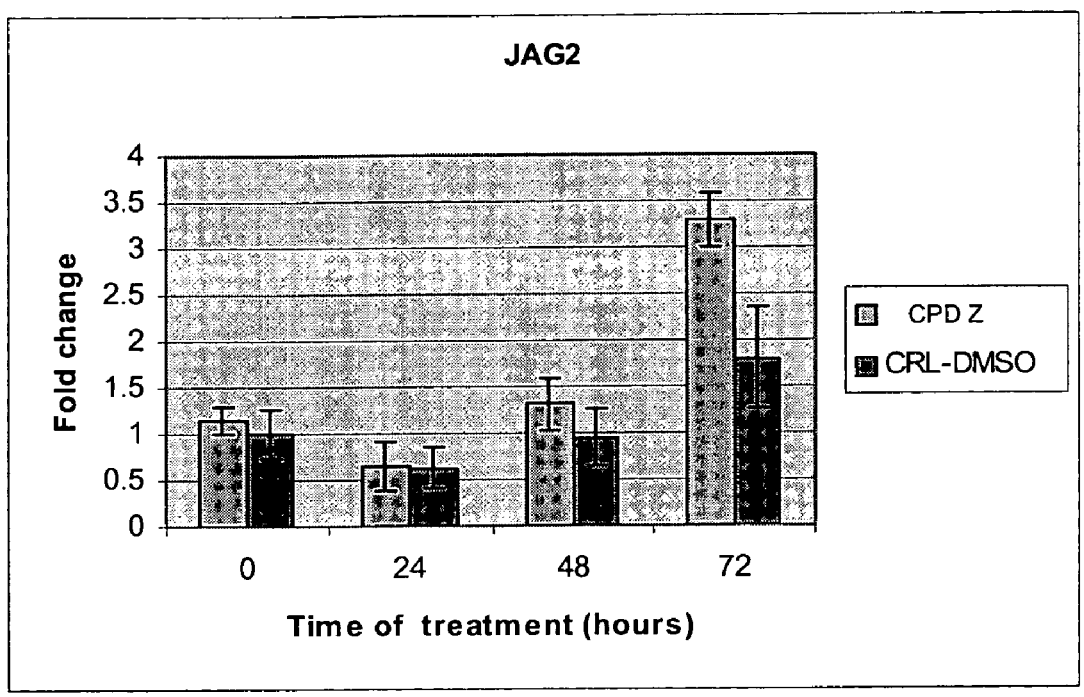
Figure 5D:
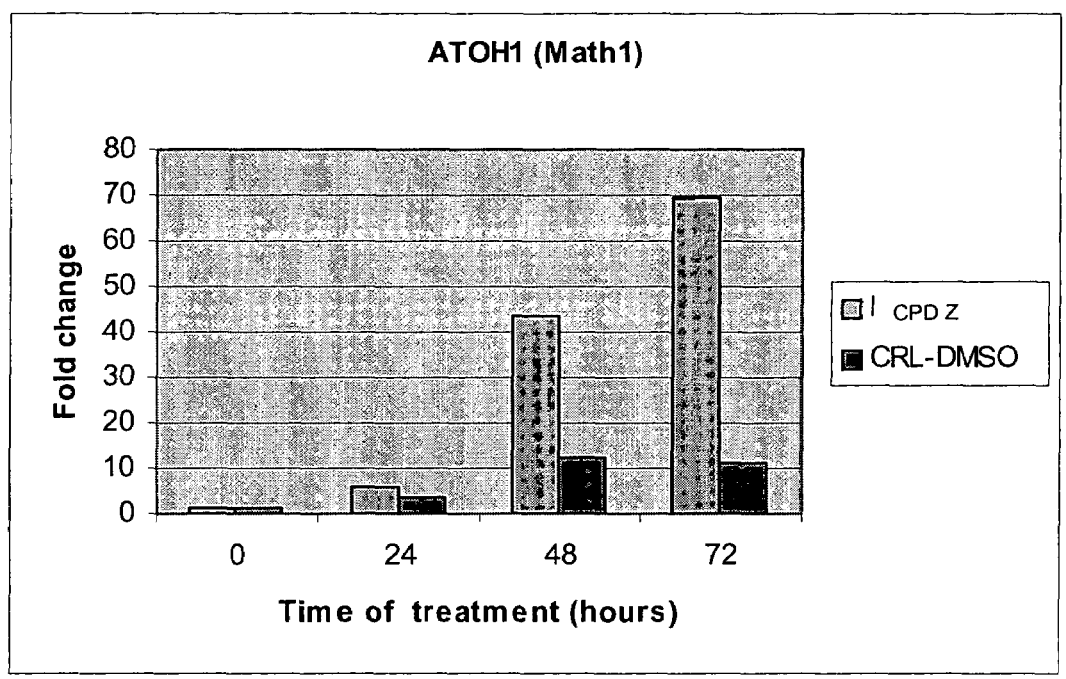
Figure 5E:
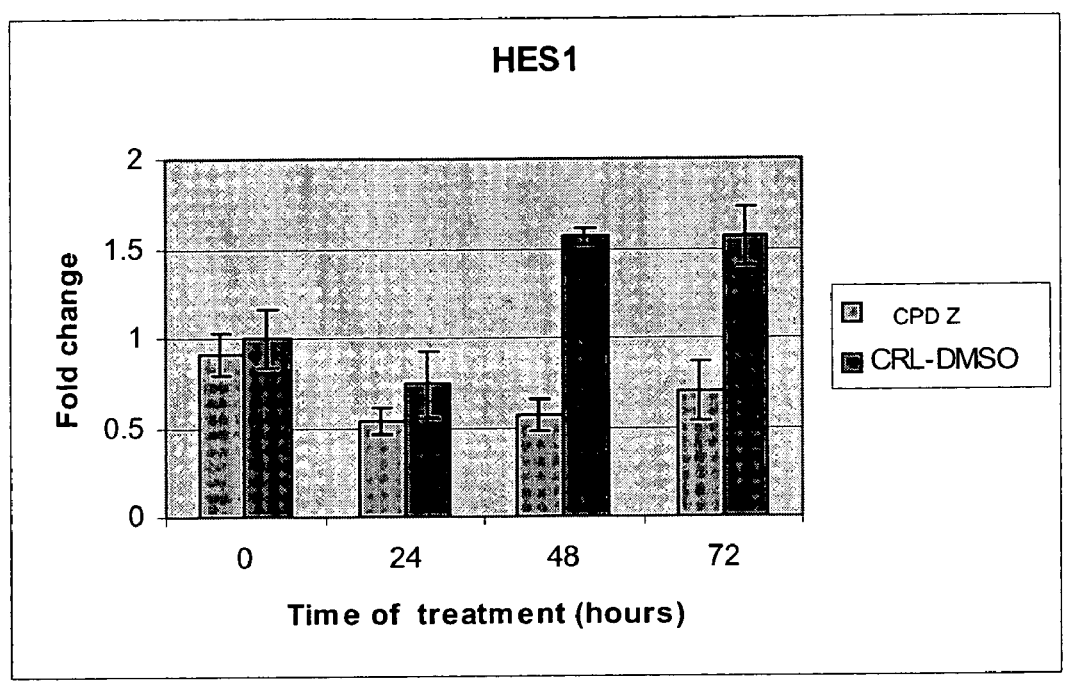

Compound Z treatment induced the goblet cell marker Mucin-2 (FIG. 5A), Notch ligands Delta-1(FIG. 5B) and Jagged-2 (FIG. 5C), and the Notch pathway gene Math-1 (FIG. 5D). The Notch pathway gene HES-1 was downregulated (FIG. 5E).

Example 5

Activated Notch Expression Prevents Mucin-2 Induction by Notch Cleavage Inhibitor HT29-L23 cells were transiently transfected with control plasmid (pcDNA-DsRed) or Myc epitope tagged Notch intracellular domain (NICD) (activated Notch-1) or APP intracellular domain (AICD) (activated APP). Cells were treated with Compound Z (1 uM in DMSO) or vehicle, and protein expression was analyzed by High Content Screening as described in Example 1. After staining with Mucin-2 and Myc antibodies, the transfected subpopulation of cells (Myc positive) were used for final analysis. Cells without DsRed expression were designated as control. Statistical significance was determined by one-way ANOVA followed by Bonferroni's multiple comparison test performed within and between groups.

Figure 6:
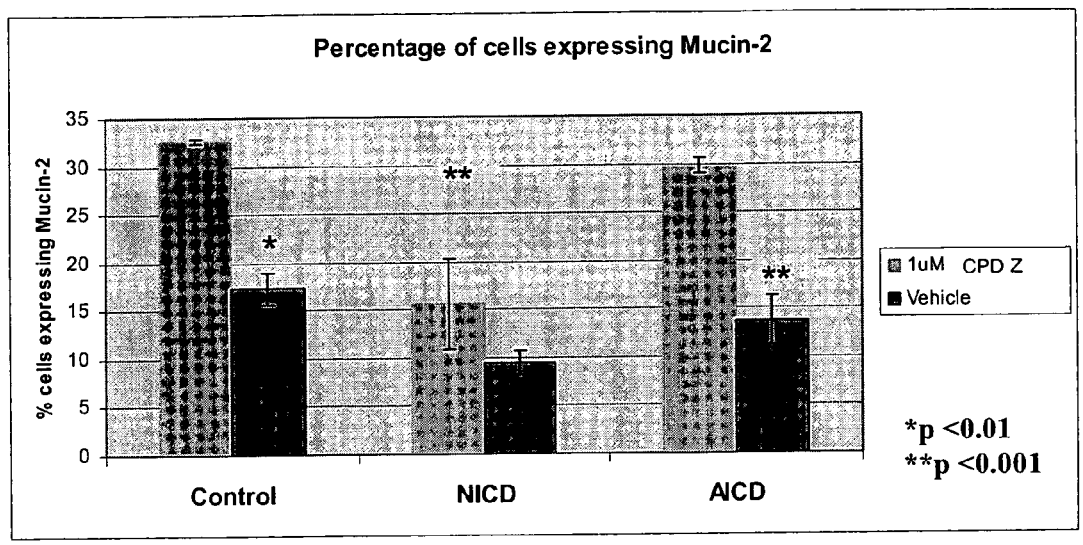
FIG. 6 demonstrates that activated Notch expression prevents induction of mucin-2 by a γ-secretase/Notch cleavage inhibitor.

The number of cells producing mucin-2 increased after treatment with Compound Z in the Control and AICD groups but not in the NICD group (FIG. 6).

Example 6

Assay for Mucin-2 Induction

Figure 7A:
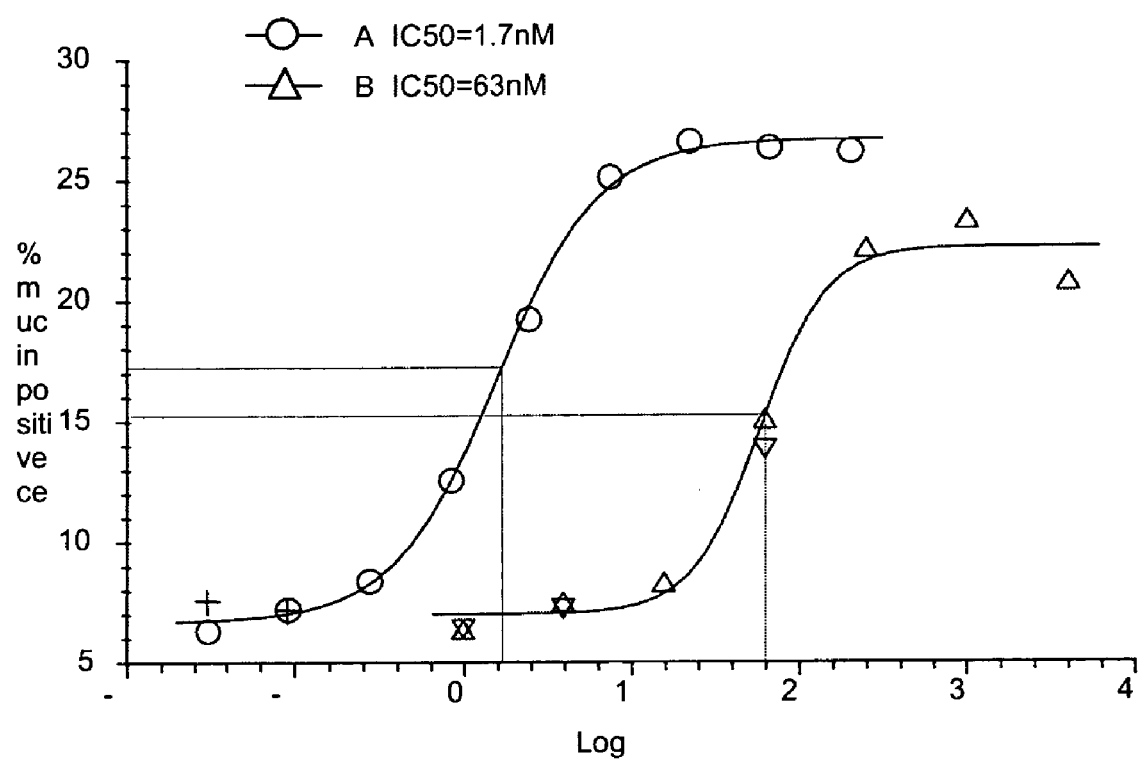
FIGS. 7A and 7B illustrate mucin-2 induction in HT29-L23 cells by γ-secretase inhibitors A and B as detected by FACS (FIG. 7A) and high content screening (FIG. 7B).
Figure 7B:
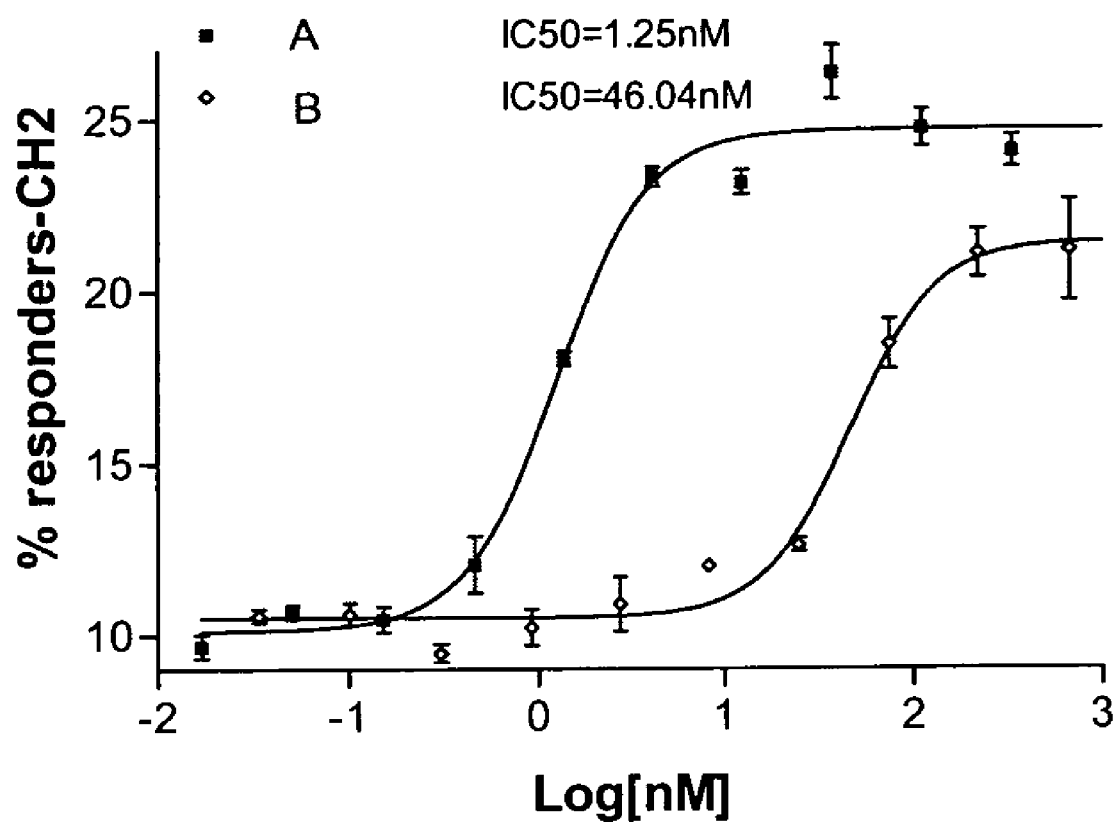

HT29-L23 cells were treated with γ-secretase inhibitor compounds A or B. Mucin-2 induction in HT29-L23 cells by γ-secretase inhibitors A and B as detected by FACS (FIG. 7A) and high content screening (FIG. 7B).

Example 7

Duodenal Histopathology

Rats or dogs were orally dosed by gavage QD or BID for 72 hr with a toxic γ-secretase inhibitor which inhibits Notch. Five hours after the last dose, animals were sacrificed, duodenum collected and gently washed with PBS. Tissues were sectioned, fixed and stained with periodic acid-Schiff (PAS) or haematoxylin/eosin (H&E). The compound-treated animals displayed intestinal goblet cell metaplasia and villus atrophy (FIG. 8B, dog; FIGS. 8D and 8E, rat) relative to untreated controls (FIG. 8A, dog; FIG. 8C, rat).

While the present invention has been particularly shown and described with reference to the presently preferred embodiments, it is understood that the invention is not limited to the embodiments specifically disclosed and exemplified herein. Numerous changes and modifications may be made to the preferred embodiment of the invention, and such changes and modifications may be made without departing from the scope and spirit of the invention as set forth in the appended claims.

What is claimed:

1. A method for identifying a compound that inhibits cleavage of Notch comprising:
    (a) contacting Notch-expressing HT29 cells with a compound that inhibits γ-secretase; and
    (b) detecting mucin-2 induction or mucin-5AC induction in said cells as compared to HT29 cells not contacted with said compound, wherein said mucin-2 induction or mucin-5AC induction is indicative of an inhibitor of Notch cleavage, and wherein the Notch-expressing cells express γ-secretase.

2. The method of claim 1 wherein said cells are preselected based on their ability to undergo mucin-2 induction or mucin-5AC induction in response to a compound known to inhibit Notch cleavage.

3. The method of claim 2 wherein said compound known to inhibit Notch cleavage is Compound Z:

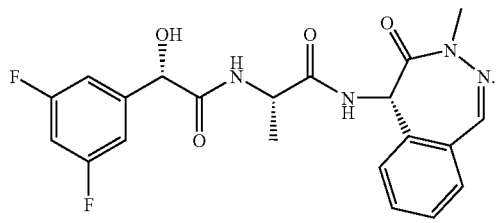

4. The method of claim 1 wherein said step of detecting comprises ELISA, flow cytometry, or a high content screening assay.

5. The method of claim 1 further comprising a step of determining whether said test compound inhibits cleavage of one or more γ-secretase substrates other than Notch.

6. The method of claim 5 wherein said γ-secretase substrate other than Notch comprises an amyloid precursor protein, an E-cadherin, a N-cadherin, LRP, Nectin-1α, CD44, ErbB4, Jagged-2, or Delta-1.

7. The method of claim 5 wherein said γ-secretase substrate other than Notch comprises an amyloid precursor protein.

8. The method of claim 5 wherein said determining step is performed prior to, after, or simultaneously with said steps (a) and (b).

* * * * *

UNITED STATES PATENT AND TRADEMARK OFFICE
CERTIFICATE OF CORRECTION

PATENT NO. : 7,608,408 B2 Page 1 of 1
APPLICATION NO. : 11/595721
DATED : October 27, 2009
INVENTOR(S) : Catherine Burton, Charles F. Albright and Judith A. Wardwell-Swanson It is certified that error appears in the above-identified patent and that said Letters Patent is hereby corrected as shown below:

Title Page, item [56] under Other Publications,

Line 1, "Gamme" should read -- Gamma --

Signed and Sealed this

Twenty-second Day of December, 2009

David J. Kappos
*Director of the United States Patent and Trademark Office*